United States Patent [19]

Miyamoto et al.

[11] Patent Number: 4,555,948

[45] Date of Patent: Dec. 3, 1985

[54] METHOD OF ULTRASONIC FLAW DETECTION OF PIPE

[75] Inventors: Hirofumi Miyamoto, Hirakata; Nobuaki Kaitatsu, Ikoma; Junichi Sugitani, Hirakata; Yasumaru Taniguchi, Osaka; Tetsuo Kaji, Himeji, all of Japan

[73] Assignees: Kubota, Ltd.; Osaka Gas Company, Limited, both of Osaka, Japan

[21] Appl. No.: 541,856

[22] Filed: Oct. 14, 1983

[51] Int. Cl.[4] ............................................. G01N 29/04
[52] U.S. Cl. ...................................................... 73/640
[58] Field of Search .................. 73/600, 637, 638, 640

[56] References Cited

U.S. PATENT DOCUMENTS 4,467,654  8/1984  Murakami et al. ................... 73/640

Primary Examiner—S. Clement Swisher
Assistant Examiner—John E. Chapman, Jr.
Attorney, Agent, or Firm—Jordan and Hamburg

[57] ABSTRACT

A method of ultrasonic flaw detection of a pipe comprises comparing ultrasonic waves passing through a test piece portion with the arithmetic means of ultrasonic waves passing through portions adjacent each side of the test portion. The comparison is made around the entire periphery of a pipe, for example, an austenic heat resisting cast steel pipe used as a hydrogen manufacturing reformer tube. This method is free from adverse influence of macrostructures unevenly distributed in the peripheral direction of the pipe, and enables a quantitative grasp of flaws in a base material and a weld of the pipe.

7 Claims, 6 Drawing Figures

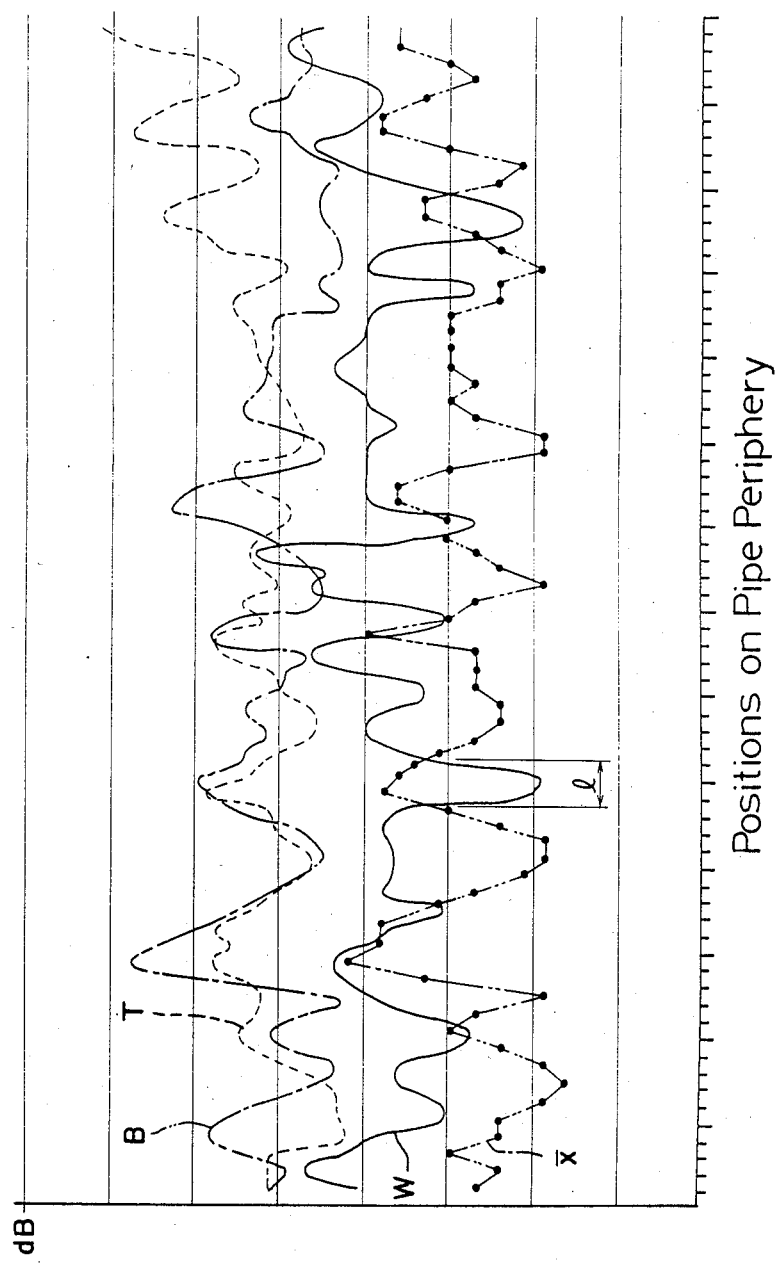

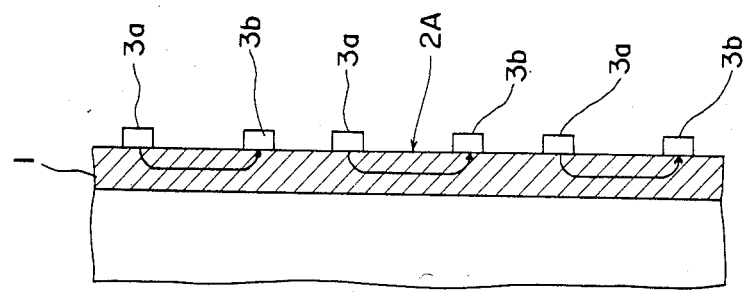
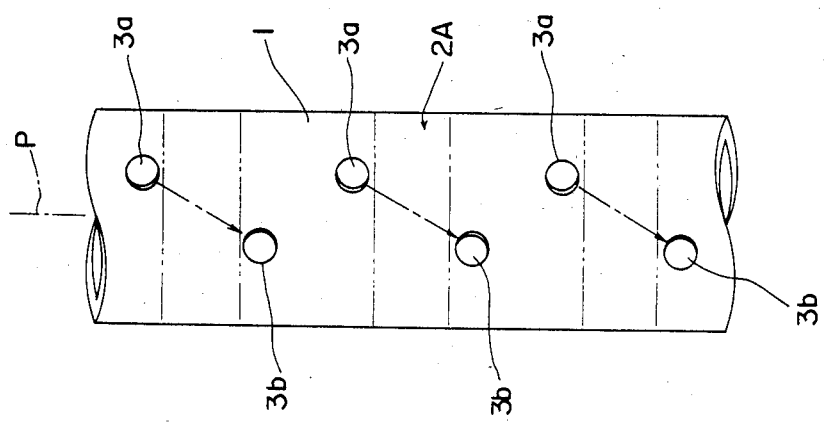

METHOD OF ULTRASONIC FLAW DETECTION OF PIPE

BACKGROUND OF THE INVENTION

This invention relates to a method of ultrasonic flaw detection of a pipe to detect flaws in a base material and a weld of the pipe by transmitting ultrasonic waves therethrough. The method is applicable to reactor pipes at a chemical plant such as a hydrogen manufacturing reformer tube, and to other pipes used for varied functions.

The method of ultrasonic flaw detection of a pipe according to the prior art, generally, is explained with reference to FIG. 1 of the present invention. As seen, an incident sound from a transmitting probe 3a mounted on a pipe adjacent a test piece part 2A (which is a weld 2 in this example) is received by a receiving probe 3b mounted on the pipe adjacent and across the test piece part 2A, and whether there is a flaw in the test piece part 2A or not is determined by attenuation of the sound occurring as it traverses the test piece part 2A. With such a flaw detection method, however, the attenuation of the sound is affected by macrostructures, surface roughness and the like of the pipe, and is received in an affected state by the receiving probe 3b to measure its decibel value, which results in a very low degree of detecting precision.

In order to eliminate the above disadvantage, a method as explained with reference to FIGS. 2 and 3 of the invention has been proposed, in which the decibel values of through-transmission sounds as received are measured using the transmitting probe 3a and the receiving probe 3b at two pipe positions opposite to each other relative to the test piece part 2A, and an arithmetic mean of these decibel values is compared with a decibel value of a through-transmission sound obtained at the test piece part 2A, a difference therebetween providing a basis for determining presence of a flaw. This method is effective to offset the adverse influence of marcrostructures, surface roughness and the like of the pipe and to detect flaws with a relatively high precision. However, according to this method, the arithmetic mean of the decibel values of the received sounds measured at two positions adjacent the test piece part 2A (i.e. only one position at each side of the test piece part 2A) is regarded as the mean value throughout an entire periphery of the pipe. Therefore, this method after all lacks in detecting precision when applied to pipes whose macrostructures and surface roughness are uneven in the peripheral direction.

To be particular, an austenic heat resisting cast steel pipe to be used as a steam catalytic reforming heater pipe, for example, which is usually made by centrifugal casting has macrostructures distributed quite unevenly not only in the axial direction but in the peripheral direction also. Since the foregoing method carries out flaw detection without regard to such a peripheral distribution of macrostructures, it is impossible to detect flaws with a truly good precision or to provide a quantitative indication of tendencies of the flaws.

SUMMARY OF THE INVENTION

The object of this invention is to eliminate the foregoing disadvantages of the prior art methods and to provide a novel and useful flaw detecting method capable of high precision flaw detection even for austenic heat resisting cast steel pipes and the like and of providing a quantitative indication of tendencies of the flaws.

In order to achieve the above object, a method of ultrasonic flaw detection of a pipe according to this invention comprises the steps of measuring decibel values T(dB) and B(dB) of the ultrasonic waves received after being transmitted through the pipe continuously or intermittently over entire peripheries of the pipe adjacent both sides of the test piece part, measuring a decibel value W(dB) of the ultrasonic wave received after being transmitted through the pipe continuously or intermittently over an entire periphery of the pipe at the test piece part, and deriving a difference between an arithmetic mean of the decibel values T(dB) and B(dB) of the ultrasonic waves adjacent the test piece part and the decibel value W(dB) of the ultrasonic wave at the test piece part at a particular phase in the peripheral direction of the pipe, continuously or intermittently over the entire periphery of the pipe, to determine flaw developing tendencies in the test piece part on the basis of variations of the difference in the peripheral direction of the pipe.

According to this method as described above, ultrasonic waves are transmitted though the pipe at two positions across and adjacent the test piece part to calculate an arithmetic mean of decibel values T(dB) and B(dB) of the received ultrasonic waves, and to obtain a difference between this arithmetic mean and the decibel value W(dB) of the ultrasonic wave received after having passed through the test piece part. Whether there is a flaw in the test piece part or not is determined with high precision and without adverse influence of the macrostructures and surface roughness of the pipe, on the basis of whether the difference exceeds a predetermined value or not. Particularly since the difference is obtained continuously or intermittently at very slight intervals over the entire periphery of the pipe, flaws in a pipe such as an austenic heat resisting cast steel pipe that has quite an uneven peripheral distribution of macrostructures are detected with high precision and free from the influence of the uneven distribution of the macrostructures. Furthermore, the tendency of the flaw's development in the test piece part is determined on the basis of how the above difference varies in the peripheral direction of the pipe according to, for example, a peripheral width of each flaw and a peripheral distribution of the flaws. As a result, lives of base material and weld of the pipe are predicted very accurately, whereby trouble such as leakage is now effectively prevented.

Other objects and advantages of this invention will be apparent from the following description.

BRIEF DESCRIPTION OF THE DRAWINGS

FIG. 4 is a graph showing detection data and how the data are processed, and FIGS. 5 and 6 are schematic front and vertically sectional views, respectively, showing a flaw detection mode wherein the test piece part comprises a base material portion of a pipe.

DESCRIPTION OF THE PREFERRED EMBODIMENTS

An embodiment of the invention in which a weld 2 is formed in a test piece part 2A, is described with reference to FIGS. 1-4.

Figure 1:
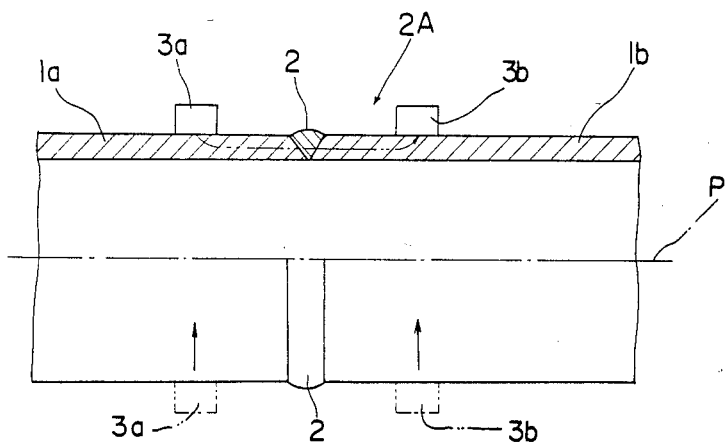
FIGS. 1–3 are schematic sectional views showing flaw detection modes wherein the test piece part comprises a weld.

As shown in FIG. 1, a transmitting probe 3a and a receiving probe 3b are set across a weld 2 connecting pipes 1a and 1b end to end. The two probes 3a and 3b are moved at the same rate peripherally of the pipes while causing an ultrasonic wave to traverse the weld 2 at an angle to a pipe axis P. A correlation between variations in flaw detecting positions in the peripheral direction of the pipe and variations in saturated decibel value W(dB) of the ultrasonic wave received by the receiving probe 3b is automatically and continuously recorded in a solid line on a graph as shown in FIG. 4.

Figure 2:
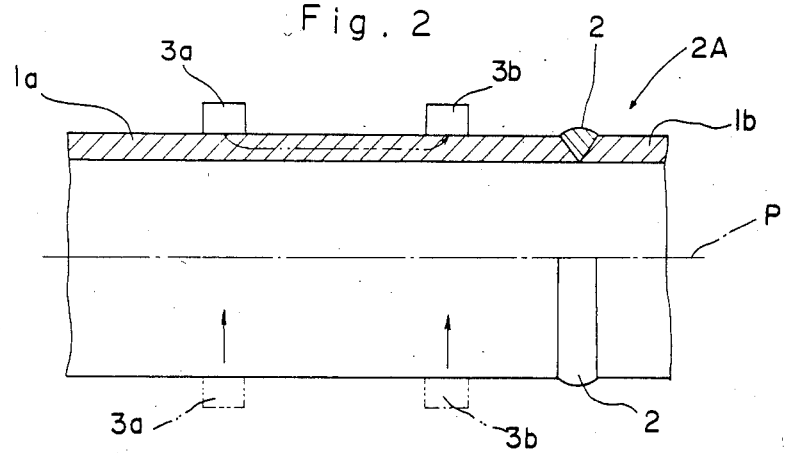

As shown in FIG. 2, the transmitting probe 3a and the receiving probe 3b are set on the upper pipe 1a adjacent the weld 2, and the two probes 3a and 3b are moved at the same rate peripherally of the pipe while transmitting an ultrasonic wave through the pipe at an angle to the pipe axis P. A correlation between variations in flaw detecting positions in the peripheral direction of the pipe and variations in saturated decibel value T(dB) of the ultrasonic wave received by the receiving probe 3b is automatically and continuously recorded in a dotted line on the graph as shown in FIG. 4.

Figure 3:
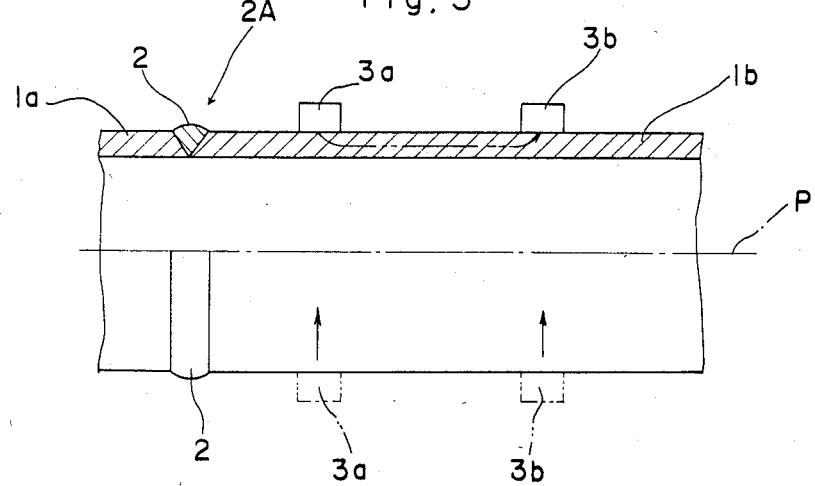

As shown in FIG. 3, the transmitting probe 3a and the receiving probe 3b are set on the lower pipe 1b adjacent the weld 2, and the two probes 3a and 3b are moved at the same rate peripherally of the pipe while transmitting an ultrasonic wave through the pipe at an angle to the pipe axis P. A correlation between variations in flaw detecting positions in the peripheral direction of the pipe and variations in saturated decibel value B(dB) of the ultrasonic wave received by the receiving probe 3b is automatically and continuously recorded in a dot and dash line on the graph as shown in FIG. 4.

The above three flaw detecting operations may be carried out in any order or simultaneously.

Subsequently, an evaluation line $\bar{x}$ as represented by a double dot and dash line in FIG. 4 is drawn by deriving an evaluation point for each one of a great many positions at equal intervals peripherally of the pipes, from the following equation (1) which is based on the decibel values T(dB) and B(dB) taken from particular positions in the same direction of the pipes 1a and 1b:

$$Xn = \frac{Tn(\text{dB}) + Bn(\text{dB})}{2} - K \quad (1)$$

wherein n is a detecting position, and K is a constant (generally about 7.5).

Then, the line (i.e. the solid line in FIG. 4) showing variations in the decibel value W(dB) is compared with the evaluation line $\bar{x}$, and presence of a flaw is determined where the decibel value W(dB) is lower than the evaluation line $\bar{x}$. At the same time, flaw developing tendencies are grapsed quantitatively on the basis of each flaw width l and the flaw distribution in the peripheral direction of the pipes, whereby the life of the weld 2 is predicted.

A further embodiment in which the base material of a pipe 1 is the test piece part 2A, is hereinafter described with reference to FIGS. 5 and 6.

First, the transmitting probe 3a and the receiving probe 3b are set to the object pipe 1 at an angle to the axis P thereof, and the two probes 3a and 3b are moved in the above positional relationship at the same rate along the axis P of the pipe 1, in search of flaws. If the decibel value of the received ultrasonic wave drops at a certain part of the base material of the pipe 1, this part makes the test piece part 2A. Then, as in the foregoing example, the two probes 3a and 3b are divided across the test piece part 2A and at an angle to the axis P, and moved together at the same rate peripherally of the pipe 1. A correlation between flaw detecting positions in the peripheral direction of the pipe 1 and variations in saturated decibel value W(dB) of the ultrasonic wave received by the receiving probe 3b is automatically and continuously recorded on a graph. Further, as in the foregoing embodiment, the transmitting probe 3a and the receiving probe 3b are set adjacent each side of the test piece part 2A and at an angle to the axis P, and moved together at the same rate peripherally of the pipe 1. Correlations between flaw detecting positions in the peripheral direction of the pipe 1 and variations in saturated decibel values T(dB) and B(dB) of the ultrasonic wave received by the receiving probe 3b are automatically and continuously recorded on the graph. An evaluation line $\bar{x}$ is drawn on the basis of the equation (1) and is compared with the line showing variations in the decibel value W(dB). Thus, flaw developing tendencies are grasped quantitatively on the basis of each flaw width l and flaw distribution in the peripheral direction of the pipe 1, whereby the life of the base material is predicted.

For moving the transmitting probe 3a and the receiving probe 3b peripherally or axially of the pipes together, it is a common practice to provide a holder having a rotational drive means in order to set the probes 3a and 3b to the pipes 1a, 1b and 1 and automatically move the proves 3a and 3b at the same rate. The specific construction therefor is variable as desired. The probes 3a and 3b may be moved manually at the same rate. Further, the probes 3a and 3b may be moved automatically or manually at very slight intervals, taking flaw detection data at stops.

The flaw detection data may be processed, for example, by deriving evaluation points Xn from the equation (2) set out below, and deciding that there are flaws where the evaluation points Xn are minus. Any other equation may be used from which the difference between the arithmetic mean of the measured decibel values T(dB) and b(dB) of the pipes 1a, 1b and 1 and the measured decibel value W(dB) of the test piece part 2A such as weld 2 is derived. Further, it will be of practical advantage to process the detection data on a computer and to record data necessary for determining flaws.

$$Xn = W - [(Tn+Bn)/2 - K] \quad (2)$$

The described method of ultrasonic flaw detection according to this invention is applicable to any types of pipe and ultrasonic flaw detecting apparatus to be used therefor is variable in its specific construction.

We claim:

1. A method of ultrasonic flaw detection of a pipe with a test piece part therein by means of ultrasonic waves applied onto the pipe, comprising:
   measuring decibel values T(dB) of ultrasonic waves around the entire periphery of the pipe at one side adjacent to the test piece part, measuring decibel values B(dB) of ultrasonic waves around the entire periphery of the pipe at the other side adjacent to the test piece part, measuring decibel values W(dB) of ultrasonic waves passing through the test piece part around the entire periphery of the pipe, establishing the arithmetic mean of the decibel values T(dB) and B(dB) as a function of position around the pipe by following equation (1):

$$Xn = \frac{Tn(dB) + Bn(dB)}{2} - K \qquad (1)$$

wherein n is a position around the pipe, and K is a constant, and deriving the difference between the arithmetic mean obtained by the equation (1) and the decibel value W(dB) at the test piece part around the periphery of the pipe, the difference being measured around the entire periphery of the pipe to determine flaw developing tendencies in the test piece part on the basis of variations of the difference.

2. A method of ultrasonic flaw detection of a pipe as defined in claim 1, wherein the step of deriving the difference comprises drawing an evaluation line X of the arithmetic mean based on the equation (1), drawing a line W by plotting the decibel values W(dB), and comparing the arithmetic mean in the evaluation line X and the decibel value W(dB) in the line W around the entire periphery of the pipe.

3. A method of ultrasonic flaw detection of a pipe as defined in claim 2, wherein each step of measuring decibel values comprises emitting ultrasonic waves from a source onto the pipe, receiving and recording the ultrasonic waves transferred through the pipe from the source at a predetermined point away from the source, and moving the emitting and receiving points of ultrasonic waves around the entire periphery of the pipe.

4. A method of ultrasonic flaw detection as defined in claim 3, wherein the pipe comprises an austenic heat resisting cast steel pipe.

5. A method of ultrasonic flaw detection as defined in claim 4. wherein the test piece part comprises a weld interconnecting pipes end to end.

6. A method of ultrasonic flaw detection as defined in claim 4, wherein the test piece part comprises a base material of the pipe.

7. A method of ultrasonic flaw detection as defined in claim 6, further comprising a step of searching flaws in the axial direction of the pipe beforehand in order to determine the test piece part.

* * * * *